(12) United States Patent
Kim et al.

(10) Patent No.: US 10,299,806 B2
(45) Date of Patent: May 28, 2019

(54) BONE CLAMP

(71) Applicants: Alexander D. Kim, Boston, MA (US); David C. Kim, Boston, MA (US)

(72) Inventors: Alexander D. Kim, Boston, MA (US); David C. Kim, Boston, MA (US)

( * ) Notice: Subject to any disclaimer, the term of this patent is extended or adjusted under 35 U.S.C. 154(b) by 177 days.

(21) Appl. No.: 14/999,030

(22) Filed: Mar. 21, 2016

(65) Prior Publication Data

US 2017/0265880 A1 Sep. 21, 2017

(51) Int. Cl.
*A61B 17/17* (2006.01)
*A61B 17/88* (2006.01)

(52) U.S. Cl.
CPC .......... *A61B 17/17* (2013.01); *A61B 17/8866* (2013.01)

(58) Field of Classification Search
CPC ..... A61B 17/28–285; A61B 2017/2808–2845; A61B 17/29–295; A61B 2017/2901–2948; A61B 17/8866
USPC ........................................................ 606/324
See application file for complete search history.

(56) References Cited

U.S. PATENT DOCUMENTS

| | | | | |
|---|---|---|---|---|
| 1,217,637 A * | 2/1917 | Rink | ..................... | A61B 17/155 606/76 |
| 2,181,746 A * | 11/1939 | Siebrandt | ............... | A61B 17/17 408/115 R |
| 3,835,849 A * | 9/1974 | McGuire | ............ | A61B 17/1739 606/96 |
| 4,364,381 A * | 12/1982 | Sher | ...................... | A61B 17/176 606/916 |
| 5,725,532 A | 3/1998 | Shoemaker | | |
| 9,770,764 B1 * | 9/2017 | Schmier-II | .............. | B23B 49/00 |
| 2008/0009871 A1 | 1/2008 | Orbay et al. | | |
| 2008/0287985 A1 * | 11/2008 | Patterson | ........... | A61B 17/2833 606/208 |
| 2009/0254130 A1 | 10/2009 | Wotton, III | | |
| 2011/0224734 A1 * | 9/2011 | Schelling | ........... | A61B 17/7079 606/286 |
| 2012/0035611 A1 * | 2/2012 | Kave | ................... | A61B 17/7074 606/102 |
| 2014/0031882 A1 * | 1/2014 | Schmuck | ............... | A61B 17/68 606/324 |
| 2015/0313640 A1 * | 11/2015 | O'Daly | ................... | A61B 17/56 606/86 R |

\* cited by examiner

*Primary Examiner* — Matthew J Lawson
(74) *Attorney, Agent, or Firm* — Timothy S. Stevens (57) ABSTRACT

A bone clamp having a first jaw, an opposed second jaw and a drill guide, the drill guide being attached to the first jaw so that bone held between the first jaw and the second jaw can be drilled by a drill inserted through the drill guide, the first jaw having a longitudinal axis. The drill guide can be ball shaped at one distal end thereof that is positioned sufficiently within and retained within a corresponding cavity of the first jaw so that the angle of the drill guide can be adjusted to compound angles in the longitudinal and transverse directions in relation to the longitudinal axis of the first jaw. The bone clamp preferably comprises an organic polymer that is relatively transparent to X-rays.

7 Claims, 12 Drawing Sheets

BONE CLAMP

BACKGROUND OF THE INVENTION

The instant invention relates to surgical instruments and more particularly to bone clamping devices. Even more particularly, the instant invention relates to bone clamps having guides for guiding bone drills so that a fractured bone can be temporarily held in place when drilled to produce a drilled passageway in the fractured bone followed by the insertion of a bone screw into the drilled passageway to permanently secure the fractured bone.

A number of bone clamp designs are available to the modern orthopedic surgeon. U.S. Pat. No. 5,725,532 to Shoemaker disclosed a locking forceps design having a fixed drill guide in one jaw thereof. U.S. Pat. No. 8,080,045 to Wotton, III, disclosed a locking forceps design having a fixed drill guide in a coaxially articulated jaw arrangement. U.S. Pat. No. 3,835,849 to McGuire discloses a c-clamp design having a sliding drill guide in one jaw thereof. USPAP 2008/0009871 of Orbay et al. discloses a c-clamp design having a drill guide bored axially through the clamping screw thereof as well as fixed angle drill guides in a jaw plate thereof. U.S. Pat. No. 2,181,746 to Siebrandt disclosed a locking pliers having a drill guide positioned in one jaw thereof, which drill guide could be adjusted for drilling at a number of different angles.

Despite the significant benefits provided by prior art bone clamps, none of the bone clamps of the prior art provide a drill guide having sufficient adjustment with regard to compound angles in the longitudinal and transverse directions in relation to the longitudinal axis of the jaws of the bone clamp. A bone clamp having a drill guide capable of such an adjustment would be a significant advance in the art.

SUMMARY OF THE INVENTION

The instant invention provides a solution to the above mentioned problem with prior art bone clamps. In one embodiment the instant invention is a bone clamp comprising a first jaw, an opposed second jaw and a drill guide, the drill guide being attached to the first jaw so that bone held between the first jaw and the second jaw can be drilled by a drill inserted through the drill guide, the first jaw having a longitudinal axis, wherein the improvement comprises the drill guide being ball shaped at one distal end thereof, the ball shaped end of the drill guide being positioned sufficiently within and retained within a corresponding cavity of the first jaw so that the angle of the drill guide can be adjusted to compound angles in the longitudinal and transverse directions in relation to the longitudinal axis of the first jaw.

In another embodiment the instant invention is bone clamp comprising a first jaw, an opposed second jaw, a drill guide receiver and a drill guide, the drill guide receiver being attached to the first jaw so that bone held between the first jaw and the second jaw can be drilled by a drill inserted through the drill guide attached to the drill guide receiver, the first jaw having a longitudinal axis, wherein the improvement comprises the drill guide receiver being tubular shaped and positioned within and retained within a corresponding cavity of the first jaw, the corresponding cavity of the first jaw having a longitudinal axis, the longitudinal axis of the corresponding cavity of the first jaw being aligned with the longitudinal axis of the jaw, the drill guide receiver configured to accept and retain a drill guide so that the angle of the longitudinal axis of a drill guide positioned in the drill guide receiver can be adjusted to compound angles in the longitudinal and transverse directions in relation to the longitudinal axis of the first jaw and so that the drill guide receiver can be positioned at a desired location along the longitudinal axis of the corresponding cavity of the first jaw.

DETAILED DESCRIPTION OF THE INVENTION

Figure 1:
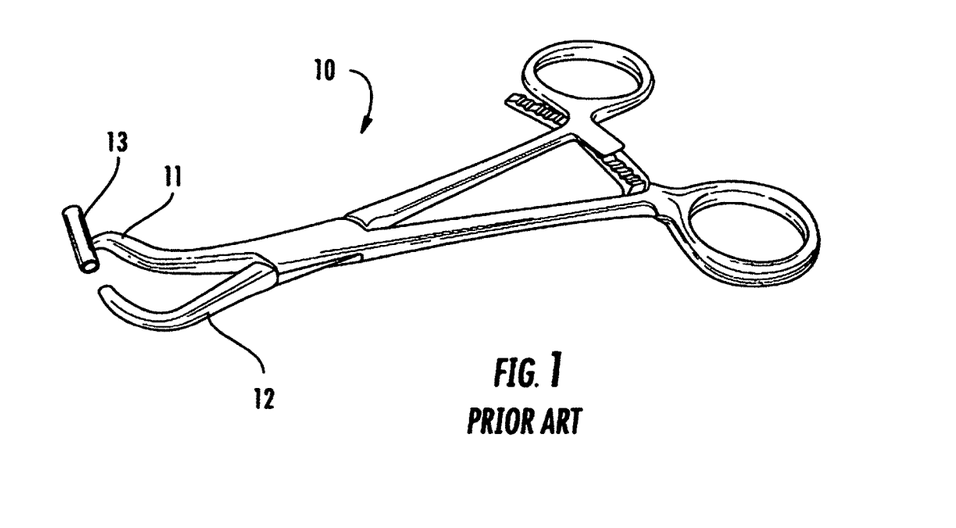
FIG. 1 is a perspective view in full of a locking forceps bone clamp of the prior art having a fixed angle drill guide attached to one jaw thereof.
Figure 2:
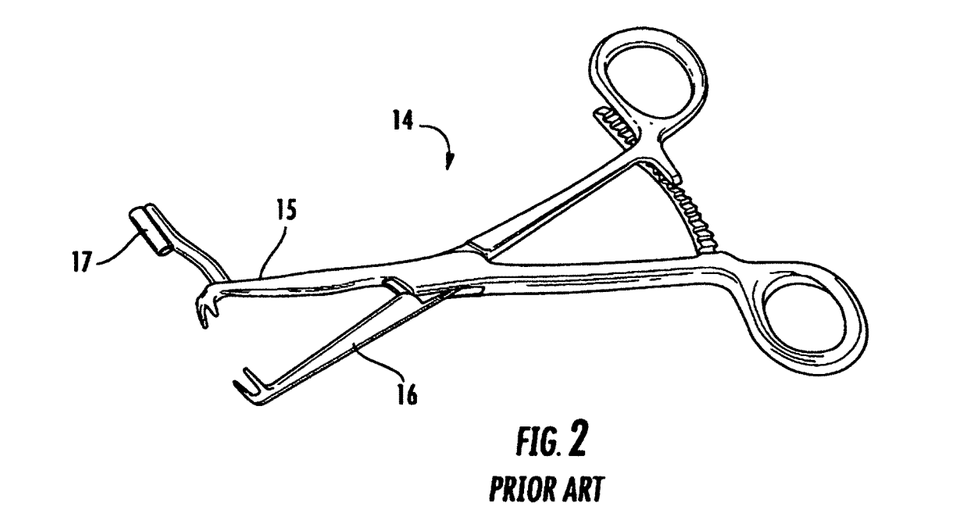
FIG. 2 is a perspective view in full of another locking forceps bone clamp of the prior art having a fixed angle drill guide attached to one jaw thereof.
Figure 3:
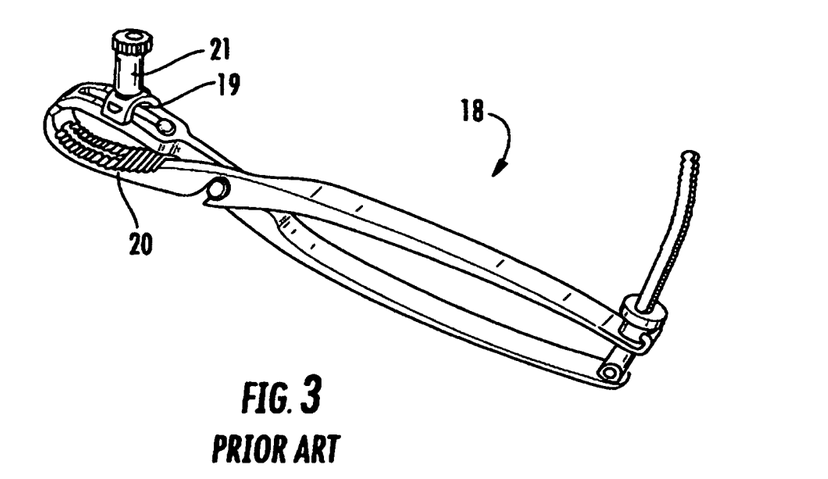
FIG. 3 is a perspective view in full of a locking pliers bone clamp of the prior art having an adjustable angle drill guide attached to one jaw thereof.
Figure 4:
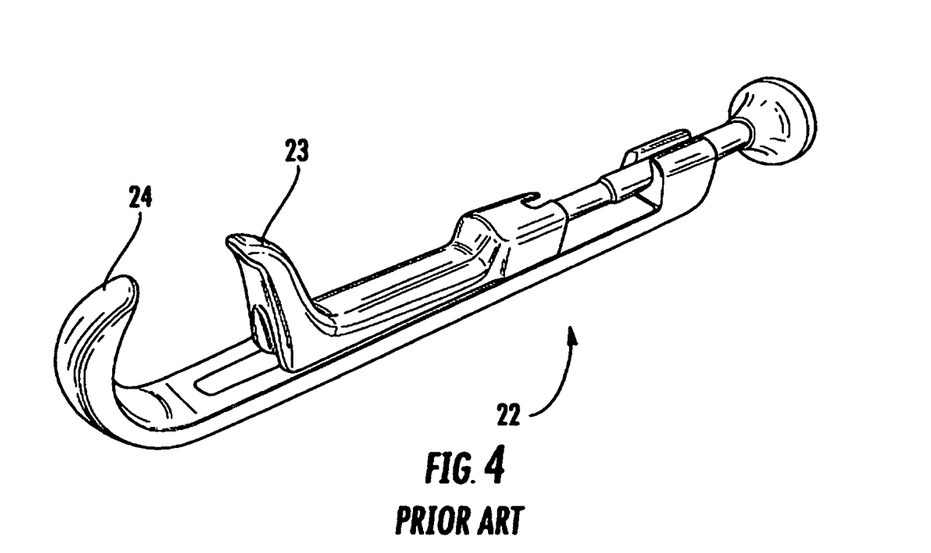
FIG. 4 is a perspective view in full of a Lowman bone clamp of the prior art having two jaws.
Figure 5:
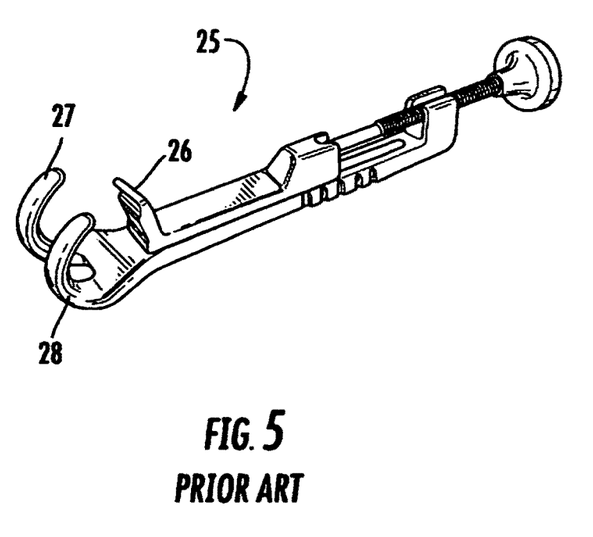
FIG. 5 is a perspective view in full of a Lowman bone clamp of the prior art having three jaws.
Figure 6:
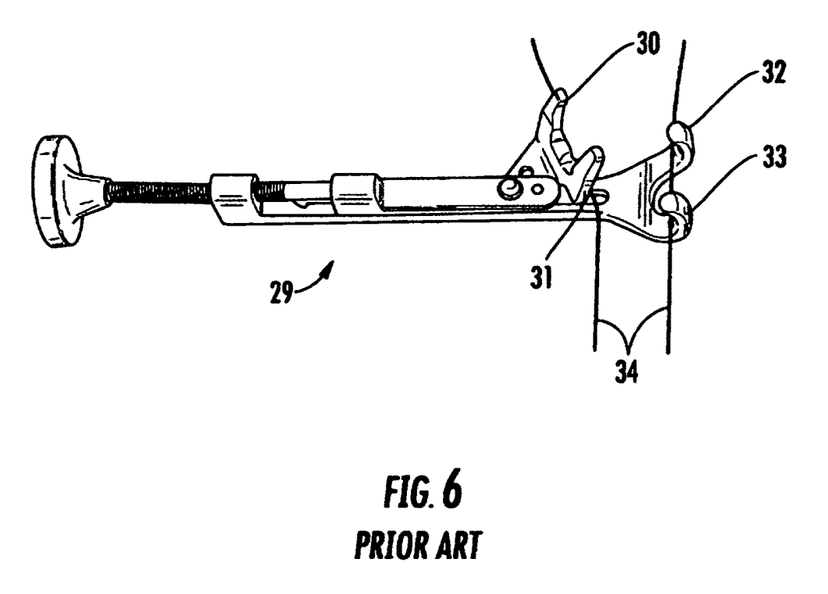
FIG. 6 is a perspective view in full of a Lowman bone clamp of the prior art having four jaws.

By way on introduction, a number of bone clamps of the prior art will be described. The instant invention is an improvement upon such prior art bone clamps. Referring now to FIG. 1, therein is shown a perspective view in full of a locking forceps bone clamp 10 of the prior art having a fixed angle drill guide 13 attached to one jaw 11 thereof, the other jaw 12 thereof having a hook shape. The bone clamp 10 is similar to the bone clamp described in U.S. Pat. No. 5,725,532 to Shoemaker. Referring now to FIG. 2, therein is shown a perspective view in full of a locking forceps bone clamp 14 of the prior art having a fixed angle drill guide 17 attached to one jaw 15 thereof, the other jaw 16 thereof terminating in a toothed shape. Referring now to FIG. 3, therein is shown a perspective view in full of a locking pliers bone clamp 18 of the prior art having an adjustable angle drill guide 21 attached to one jaw 19 thereof, the other jaw 20 thereof having a conventional pliers shape. The bone clamp 18 is disclosed in U.S. Pat. No. 2,181,746. It should be understood that the drill guide 21 of the bone clamp 18 is not as adjustable in the compound angles in the longitudinal and transverse directions in relation to the longitudinal axis of the jaw 19 as the drill guide of the instant invention. Referring now to FIG. 4, therein is shown a perspective view in full of a Lowman bone clamp 22 of the prior art having two jaws 23 and 24. Referring now to FIG. 5, therein is shown a perspective view in full of a Lowman bone clamp 25 of the prior art having three jaws 26, 27 and 28. Referring now to FIG. 6, therein is shown a perspective view in full of a Lowman bone clamp 29 of the prior art having four jaws 30, 31, 32 and 33 shown grasping the outline 34 of a bone.

Figure 7:
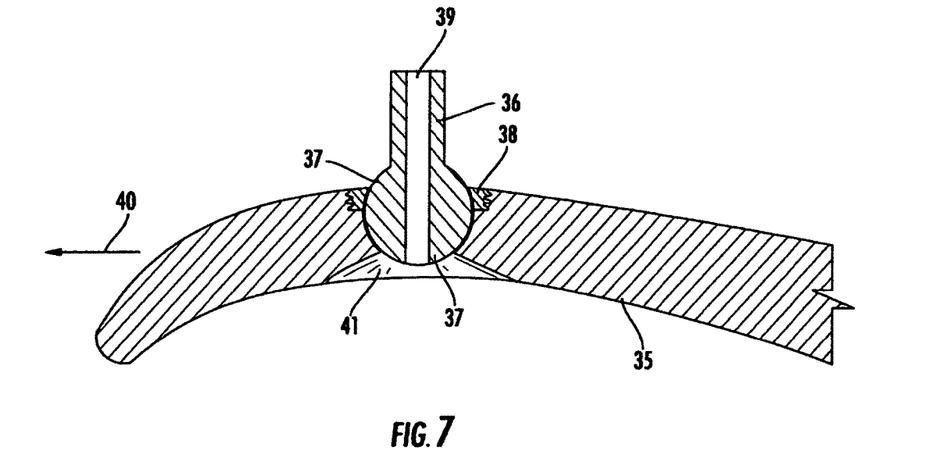
FIG. 7 is a cross-sectional broken away view of a jaw of a Lowman bone clamp incorporating an improvement of the instant invention.

The instant invention is an improvement upon prior art bone clamps that comprise at least one jaw in combination with a drill guide. In one embodiment of the instant invention the improvement comprises the drill guide being ball shaped at one distal end thereof, the ball shaped end of the drill guide being positioned sufficiently within and retained within a corresponding cavity of the jaw so that the angle of the drill guide can be adjusted to compound angles in the longitudinal and transverse directions in relation to the longitudinal axis of the jaw. Referring now to FIG. 7, therein is shown a cross-sectional broken away view of a jaw 35 of a Lowman bone clamp incorporating this improvement of the instant invention. A drill guide 36 having a ball shape 37 at one distal end is positioned within a ball shaped cavity of the jaw 35. A threaded retaining ring 38 is used to retain the ball end 37 of the drill guide 36 in the jaw 35. In a preferred embodiment, the retaining ring 38 has a knurled flange so that the retaining ring can be easily turned to tighten the drill guide at the desired angle. It will be understood that the instant invention is not limited to the use of a threaded retaining ring to retain the drill guide in the jaw and that other retention means are well known in the art. The arrow 40 is drawn in the longitudinal direction of the jaw 35. The bottom of the jaw 35 is shaped with a scallop 41 to provide clearance for a drill inserted through the bore 39 of the drill guide 36 even when the bore of the drill guide 36 is adjusted to compound angles in the longitudinal and transverse directions in relation to the longitudinal axis 40 of the jaw 35.

Figure 8:
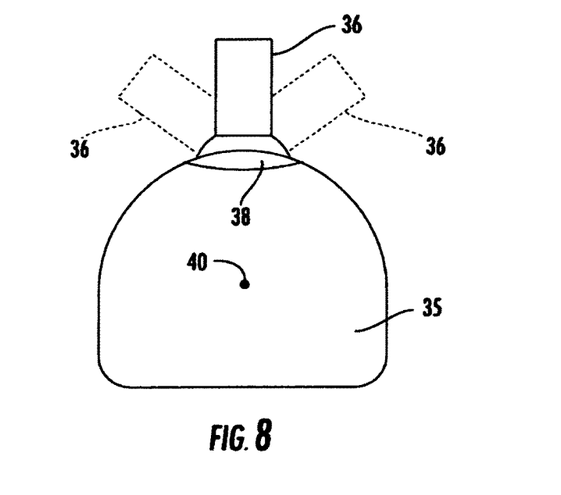
FIG. 8 is an end view in full of the jaw shown in FIG. 7.
Figure 9:
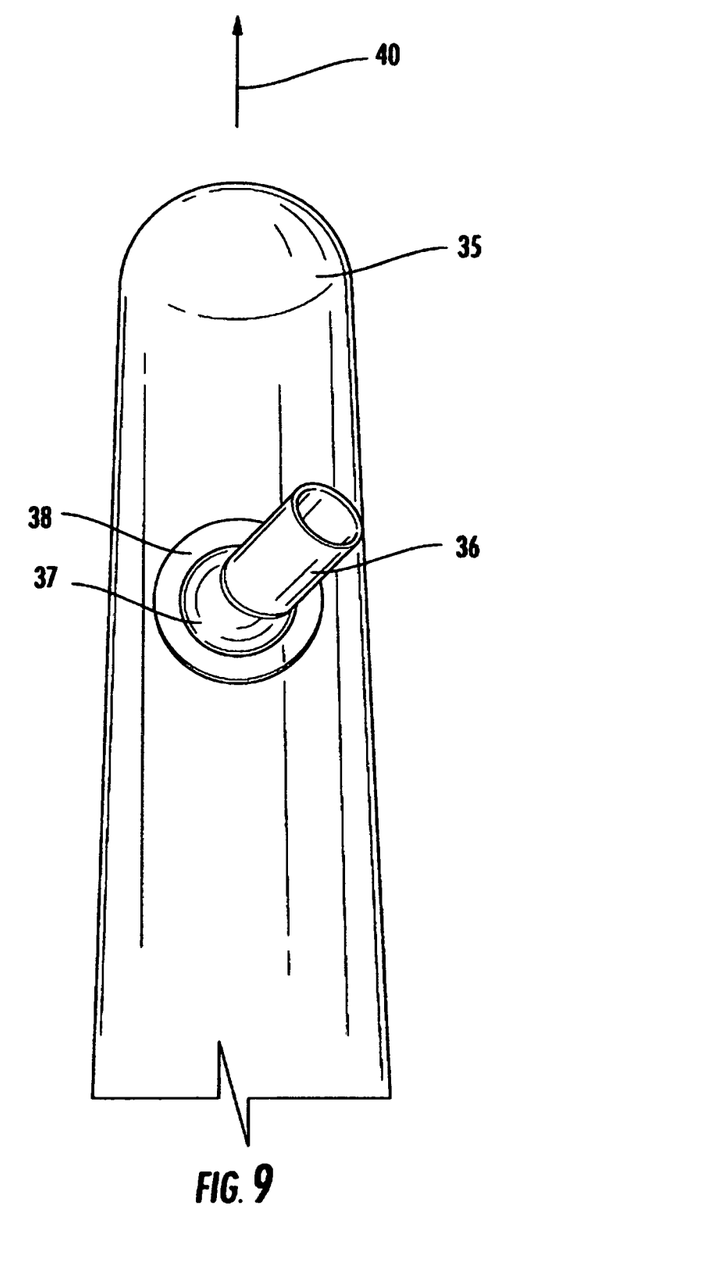
FIG. 9 is top view in full of the jaw shown in FIG. 7.

Referring now to FIG. 8, therein is shown an end view in full of the jaw 35 of FIG. 7. The drill guide 36 is shown in different transverse angles to the longitudinal axis 40 of the jaw 35. Referring now to FIG. 9, therein is shown a top view in full of the jaw 35 of FIG. 7. The drill guide 36 is shown adjusted at both a transverse and a longitudinal angle (i.e., at a compound angle) to the longitudinal axis 40 of the jaw 35. Although not shown in FIG. 9, it should be understood that the drill guide of the instant invention can be mounted in a sliding element of the jaw of the bone clamp so that the drill guide can be moved not only to compound angles in the longitudinal and transverse directions in relation to the longitudinal axis of the jaw but also back and forth in the direction of the longitudinal axis of the jaw.

Figure 10:
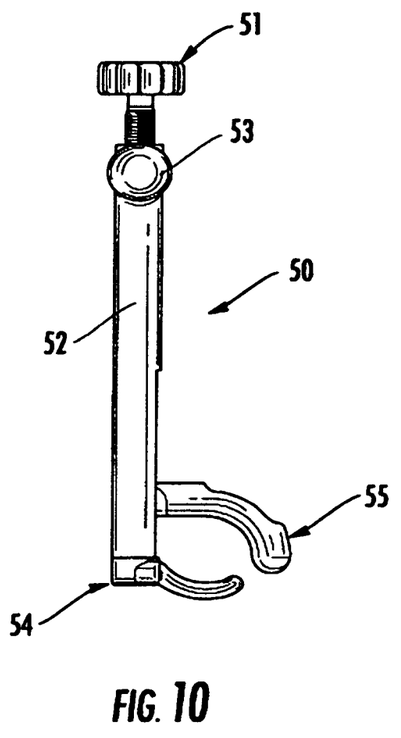
FIG. 10 is a side view in full of a Lowman bone clamp incorporating an alternative embodiment of the instant invention.
Figure 11:
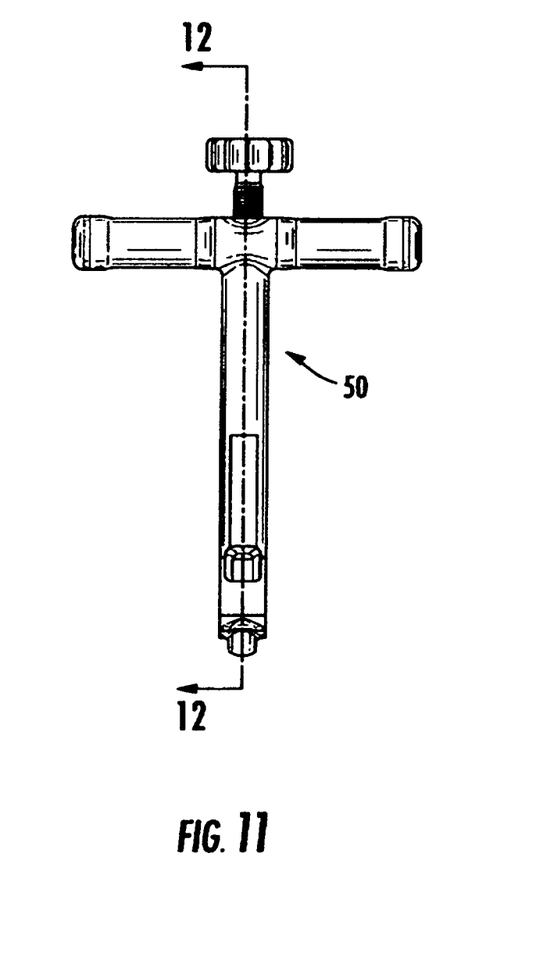
FIG. 11 is a front view of the bone clamp shown in FIG. 10 showing cross section line 12-12.
Figure 12:
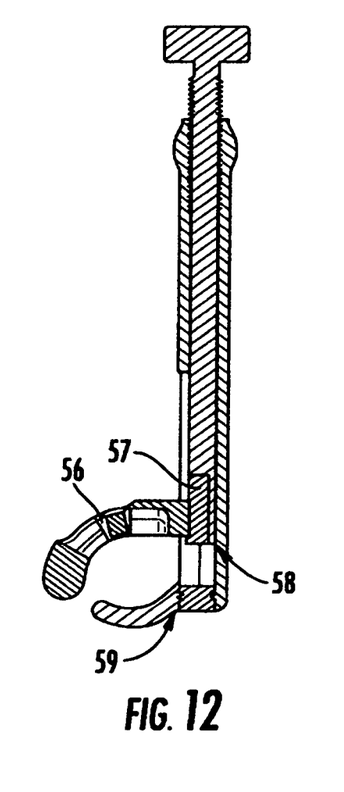
FIG. 12 is a side cross-sectional view of the bone clamp shown in FIG. 10 cross sectioned along the line 12-12 shown in FIG. 11.
Figure 13:
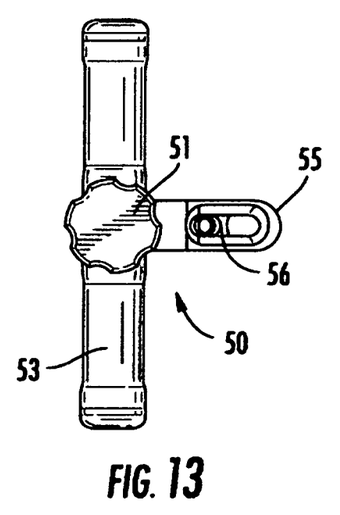
FIG. 13 is a top view in full of the bone clamp shown in FIG. 10.

Referring now to FIG. 10, therein is shown a side view in full of a highly preferred bone clamp 50 incorporating a different embodiment of the instant invention. The bone clamp 50 includes a adjusting knob 51 at the head of a threaded rod so that the knob 51 can be turned one way or the other way to move the upper jaw 55 toward or away from the lower jaw 54. The bone clamp 50 comprises a body 52 and a cross handle 53. FIG. 11 shows a front view of the bone clamp 50 and cross section line 12-12. FIG. 12 is a cross-sectional view of the bone clamp 50 cross sectioned along the line 12-12 of FIG. 11. Referring still to FIG. 12, the lower jaw of the bone clamp is attached to the body of the bone clamp by a threaded portion 59 of the end of the body. The upper jaw of the bone clamp is attached to the lower end of the threaded rod by an insert 57 having a cap end 58. A drill guide receiver 56 is shown retained within a corresponding cavity of the upper jaw, the longitudinal axis of the cavity of the jaw being aligned with the longitudinal axis of the jaw, the drill guide receiver configured to accept and retain a drill guide so that the angle of the longitudinal axis of a drill guide positioned in the drill guide receiver can be adjusted to compound angles in the longitudinal and transverse directions in relation to the longitudinal axis of the jaw and so that the drill guide receiver can be positioned at a desired location along the longitudinal axis of the cavity of the jaw. FIG. 13 shows a top view in full of the bone clamp 50 including the handle 53, the knob 51, the upper jaw 55 and the drill guide receiver 56.

Figure 14A:
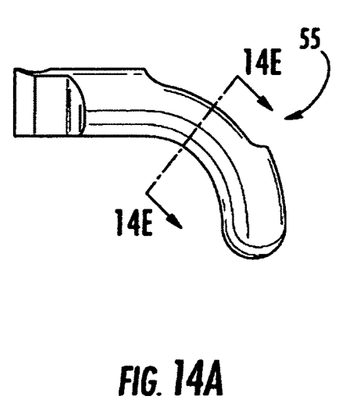
FIGS. 14A-E show various views in full and in cross section of the upper jaw of the bone clamp shown in FIG. 10.
Figure 14B:
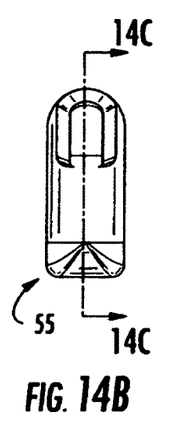
Figure 14C:
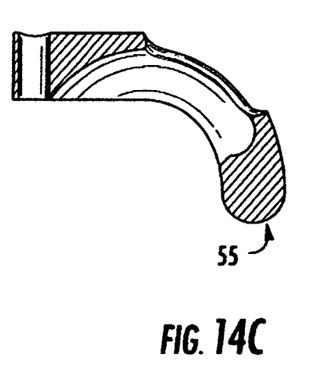
Figure 14D:
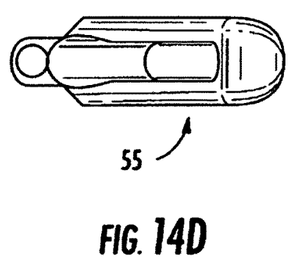
Figure 14E:
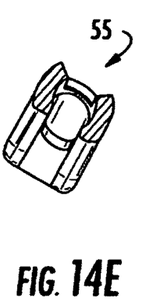
Figure 15A:
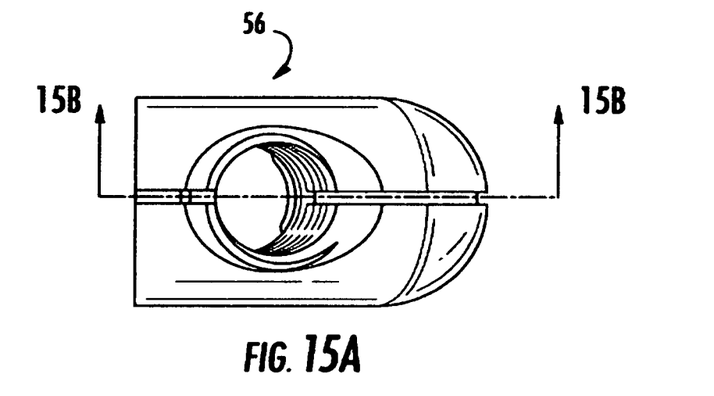
FIG. 15A shows an top view in full of a tubular shaped drill guide receiver showing cross section line 15B-15B and detailing the threaded aperture in the drill guide receiver.
Figure 15B:
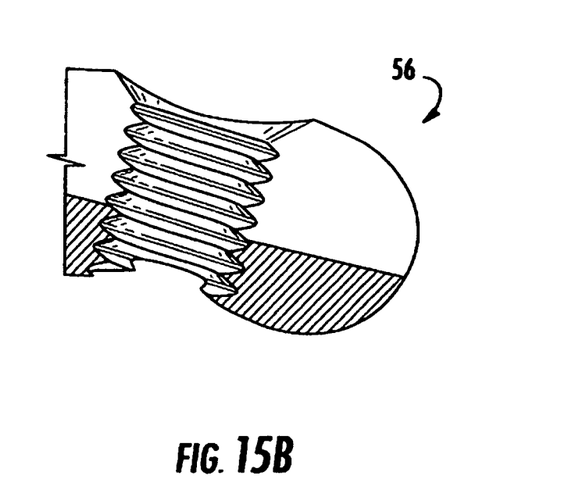
FIG. 15B is a side cross-sectional view of the drill guide receiver.
Figure 16:
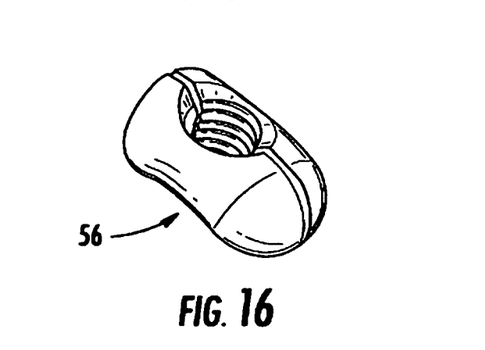
FIG. 16 shows a perspective view in full of the drill guide receiver.

Referring now to FIGS. 14A-E, therein is shown various views in full and in cross section of the upper jaw 55 of the bone clamp 50. The cross sectioned side view of the upper jaw 55 of FIG. 14C shows the drill guide receiver cavity aligned with the longitudinal axis of the upper jaw 55. The cross sectioned view of the upper jaw 55 of FIG. 14E shows the drill guide receiver cavity in an end-on view. Referring now to FIG. 15A, therein is shown a top view in full with cross section line 15B-15B and a cross-sectional side view in FIG. 15B along line 15B-15B of the drill guide receiver 56 of FIG. 15A. The drill guide receiver 56 is slotted along the top thereof to facilitate the insertion of the drill guide receiver into the drill guide receiver cavity in the upper jaw. FIG. 16 shows a perspective view in full of the drill guide receiver 56. The drill guide receiver is tubular in shape having a longitudinal axis corresponding to the longitudinal axis of the cavity in the upper jaw. It should be understood that the term "tubular" includes straight and curved tubes, that the length of the tube is not critical in the instant invention and that the term "tubular" even includes a spherical drill guide receiver.

Figure 17:
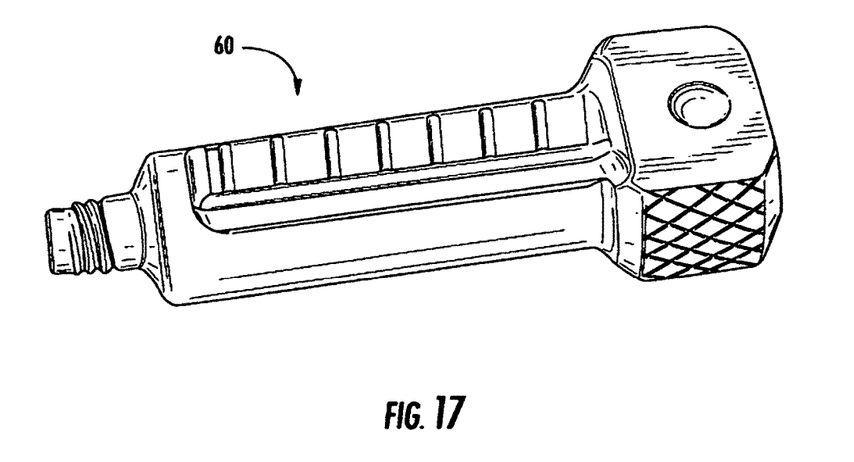
FIG. 17 shows a perspective view in full of a drill guide having a threaded end dimensioned to be mated to the threaded aperture in the drill guide receiver.
Figure 18:
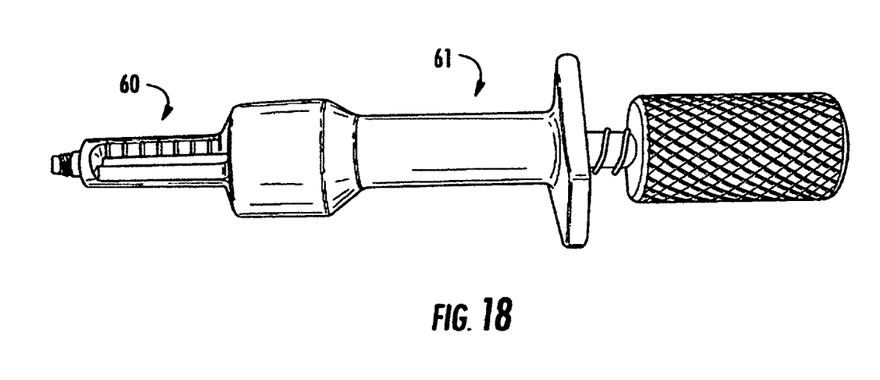
FIG. 18 shows a perspective view in full of the drill guide of FIG. 17 coupled to a drill guide installation tool.

Referring now to FIG. 17, therein is shown a perspective view in full of a drill guide 60 having a threaded end dimensioned to be mated to the threaded aperture in the drill guide receiver. Referring now to FIG. 18 therein is show a perspective view in full of the drill guide 60 of FIG. 17 coupled to a drill guide installation tool 61. In surgery, the drill guide 60 is coupled to the drill guide installation tool 61 so that the drill guide 60 can be screwed into the drill guide receiver. The drill guide can then be adjusted to compound angle in the longitudinal and transverse directions in relation to the longitudinal axis of the jaw as well as positioned at a desired location along the longitudinal axis of the cavity of the jaw to best configure the drill guide for the surgical procedure. In some embodiments of this embodiment of the instant invention, it may be preferred to integrally form the drill guide receiver with the drill guide.

It should be understood that the improvements of the instant invention can be made to any bone clamp having at least one jaw. The material of construction for the bone clamp of the instant invention can be of any suitable material such as stainless steel. However, in a preferred embodiment, the material of construction of the instant invention is an organic polymer (such as polycarbonate polymer) so that the improved bone clamp is relatively (relative to stainless steel) transparent to x-rays.

Unstable bone fractures (especially fractures of the bone(s) of the hand) require secure fixation to maximize proper healing. There are a number of methods for fixation which include pins, screws, plates and wire either singly or in combination. Screws, in particular, provide a number of advantages over other methods. In general, screw fixation requires minimal dissection which minimizes subsequent scar formation. In addition, not only do screws provide solid fixation, but the existence of the compression screw further promotes bone healing. Such screws draw the two sides of a fracture together as they traverse the bone, hence "compressing" the bone into a tighter alignment. Accurate placement of such screws is important but can be difficult given the shape of bones and the opposing forces displacing the fracture.

In use, the fractured bone is compressed and held in place with the bone clamp of the instant invention while the drill guide is aligned in a direction that will facilitate a bone screw that will be used to hold the fractured bone together during healing of the bone. A metal pin is placed through the drill guide and through the fractured bone. Proper placement of the pin is confirmed by x-ray. The length of the pin is measured, a drill is placed over the pin, the bone is drilled to the length of the pin in the bone, and then a corresponding length compression screw is placed over the pin and the pin is removed.

CONCLUSION

While the instant invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains.

What is claimed is:

1. A bone clamp comprising a first jaw, an opposed second jaw, the first jaw and the second jaw each being curved toward each other, a drill guide receiver and a drill guide, the drill guide receiver being attached to the first jaw so that bone held between the first jaw and the second jaw can be drilled by a drill inserted through the drill guide attached to the drill guide receiver, the first jaw having a longitudinal axis, wherein the improvement comprises the drill guide receiver being tubular shaped and positioned within and retained within a corresponding elongated curved cavity of the first jaw, the corresponding elongated curved cavity of the first jaw having a longitudinal axis, the longitudinal axis of the corresponding elongated curved cavity of the first jaw being aligned with the longitudinal axis of the first jaw, the drill guide receiver configured to accept and retain a drill guide so that the angle of the longitudinal axis of the drill guide positioned in the drill guide receiver can be adjusted to compound angles in the longitudinal and transverse directions in relation to the longitudinal axis of the first jaw and so that the drill guide receiver can be positioned at a desired location of a plurality of locations along the longitudinal axis of the corresponding elongated curved cavity of the first jaw.

2. The bone clamp of claim 1, wherein the bone clamp is a forceps bone clamp.

3. The bone clamp of claim 1, wherein the bone clamp is a c-clamp bone clamp.

4. The bone clamp of claim 1, wherein the bone clamp is a Lowman bone clamp.

5. The bone clamp of claim 1, wherein the bone clamp is a pliers bone clamp.

6. The bone clamp of claim 1, wherein the drill guide receiver and the drill guide are an integral unit.

7. The bone clamp of claim 1, wherein the material of construction of the bone clamp is an organic polymer.

* * * * *